United States Patent [19]

Brucks

[11] Patent Number: 4,496,341
[45] Date of Patent: Jan. 29, 1985

[54] APPARATUS FOR VAGINAL MEDICATION APPLICATION

[76] Inventor: Anton B. Brucks, 9601 Trailhill, Dallas, Tex. 75238

[21] Appl. No.: 367,167

[22] Filed: Apr. 12, 1982

[51] Int. Cl.³ ............................................. A61F 15/00
[52] U.S. Cl. ......................................... 604/14; 604/15
[58] Field of Search .................................. 604/14–18, 604/49, 54, 55

[56] References Cited

U.S. PATENT DOCUMENTS 3,424,158  1/1969  Silver ..................................... 604/54
3,749,093  7/1973  Bloom ................................... 604/14
4,035,850  7/1977  Cresswall ............................. 604/49

Primary Examiner—John D. Yasko
Assistant Examiner—Sherri Vinyard
Attorney, Agent, or Firm—Hubbard, Thurman, Turner & Tucker

[57] ABSTRACT

Apparatus is disclosed which may be utilized to package vaginal medication and may also be utilized in the application of such medication. The apparatus includes a flexible tubular membrane with an open end and a closed end. The closed end is axially depressed into the tubular membrane and forms a cavity into which the medication is placed. During packaging, a sealing cap is placed over the cavity and encloses the cavity and the medication. To utilize the apparatus for application of medication, the tubular membrane is slipped over a hollow tubular applicator and a piston member is inserted into the hollow tubular applicator. The piston member is utilized to outwardly extend the closed end of the tubular membrane and dispense the medication. After utilization, the tubular membrane is removed from the hollow tubular applicator and may be disposed of, thus preserving the sanitary condition of the applicator.

4 Claims, 4 Drawing Figures

APPARATUS FOR VAGINAL MEDICATION APPLICATION

BACKGROUND OF THE INVENTION

This invention relates in general to methods and apparatus for packaging and dispensing vaginal medications and in particular to methods and apparatus for packaging and dispensing vaginal medications which provide a higher degree of sanitation than previously known methods and apparatus.

Known methods of intravaginal application of medication typically consist of a hollow tubular applicator with an internal piston. The medication is inserted into the hollow applicator and dispensed by means of the internal piston in the manner of a large, crude hypodermic syringe. The applicators are generally constructed of plastic or cardboard materials. The cardboard applicators are typically disposable and are only utilized once. Plastic applicators are reusable and must be carefully cleaned after each application to prevent reinfection or contagion. The difficulty associated with the proper cleaning of such reusable applicators and the distaste with which most patients view this procedure are primarily responsible for a marked tendency among patients to discontinue utilization of the medication prematurely. This practice often results in the incomplete treatment of a problem which flares up again soon after treatment is discontinued. Additionally, it is common for a patient to suffer reinfection due to the incomplete disinfection of the applicator after each utilization.

Thus, when utilizing known vaginal medication applicators, a tradeoff must be made between the increased cost associated with disposable applicators and the high risk of infection and contagion associated with reusable applicators.

SUMMARY OF THE INVENTION

It is therefore one object of the present invention to provide an improved method and apparatus for dispensing vaginal medication;

it is another object of the invention to provide an improved, low-cost reusable apparatus for dispensing vaginal medications;

it is yet another object of the present invention to provide an improved, reusable apparatus for dispensing vaginal medication which significantly lowers the probability of infection or contagion;

it is another object of the present invention to provide an improved method of packaging vaginal medications.

BRIEF DESCRIPTION OF THE DRAWINGS

The novel features believed characteristic of the invention are set forth in the appended claims. The invention itself; however, as well as a preferred mode of use, further objects and advantages thereof, will best be understood by reference to the following detailed description of an illustrative embodiment when read in conjunction with the accompanying drawings, wherein:

DETAILED DESCRIPTION OF THE INVENTION

Figure 1:
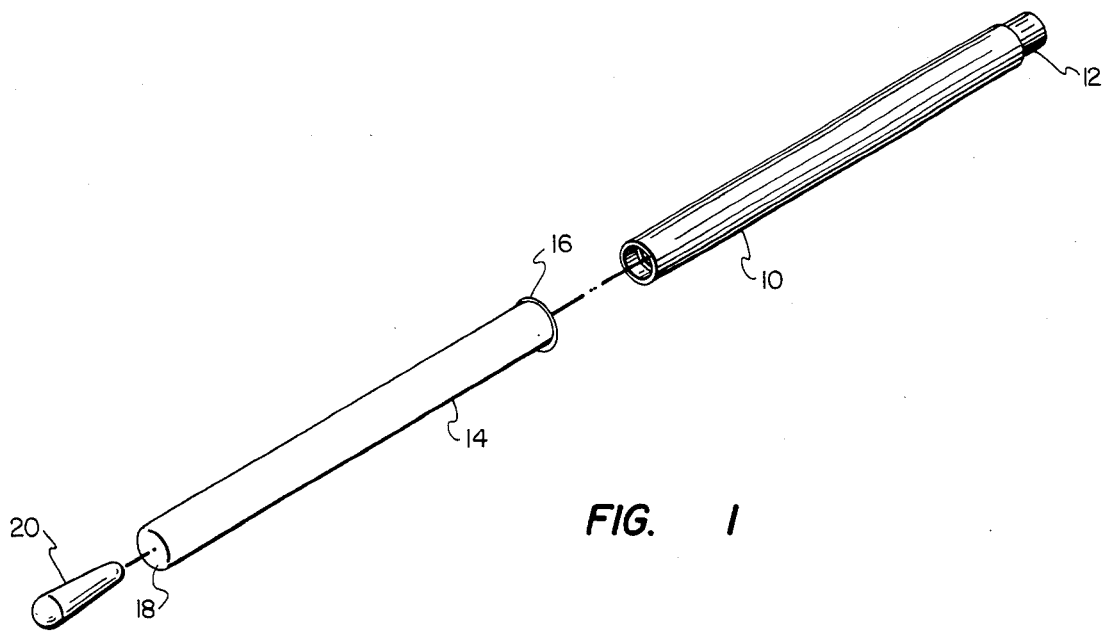
FIG. 1 is an exploded perspective view of the improved vaginal medication application apparatus of the present invention.

With reference now to the figures, and in particular with reference to FIG. 1, there is depicted an exploded perspective view of the improved vaginal medication application apparatus of the present invention. The improved vaginal medication application apparatus consists of a hollow tubular member 10 which may be constructed of any known material which provides suitable rigidity to permit vaginal insertion. Examples of suitable materials include cardboard materials, polystyrene polyethylene, polypropylene or any other known plastic material. Hollow tubular applicator 10 encloses piston means 12 which is adapted to be inserted into one end of hollow tubular applicator 10 and is utilized to dispense the selected vaginal medication.

One important aspect of the present invention is the utilization of tubular membrane 14 which is a thin, pliable tubular membrane which is adapted to be mounted in sleeved relationship with tubular applicator 10. Membrane 14 may be constructed of any material known to those skilled in the art such as a thin pliable plastic film, a latex rubber based material or a suitably impregnated paper based material. In a preferred embodiment, membrane 14 is constructed of a thin polyethylene film. Tubular membrane 14 includes an open end 16 and a closed end 18. Tubular membrane 14 is mounted in sleeved relationship with tubular applicator 10 and covers substantially the entire length of tubular applicator 10. Once tubular membrane 14 is disposed in sleeved relationship with tubular applicator 10, closed end 18 of tubular membrane 14 may be axially depressed, providing a cavity into which the vaginal medication, such as vaginal suppository 20 may be inserted.

Figure 2:
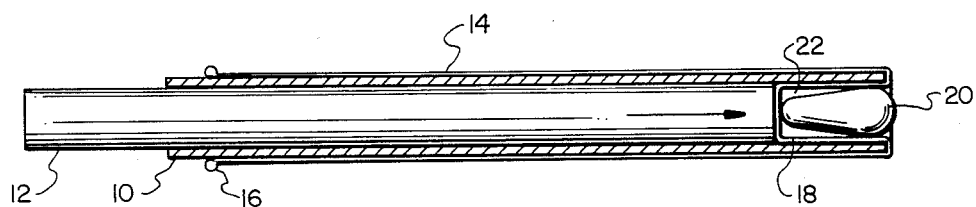
FIG. 2 is a sectional view of the improved vaginal medication application apparatus of the present invention with a vaginal suppository therein.

With reference now to FIG. 2, there is depicted a sectional view of the novel vaginal medication application apparatus of the present invention. Tubular applicator 10 is shown with piston means 12 inserted therein. Tubular membrane 14 is depicted as disposed in sleeved relationship to tubular applicator 10 with the open end 16 of tubular membrane 14 positioned near the end of tubular applicator 10, so that tubular membrane 14 covers substantially the entire length of tubular applicator 10. Closed end 18 of tubular membrane 14 is axially depressed into the open end of tubular applicator 10, forming a cavity 22 into which the desired medication may be inserted. Cavity 22, formed by the axial depression of closed end 18 of tubular membrane 14, is suitable to receive a selected amount of a selected vaginal medication, in cream, lotion or suppository form as depicted in FIG. 2.

Figure 3:
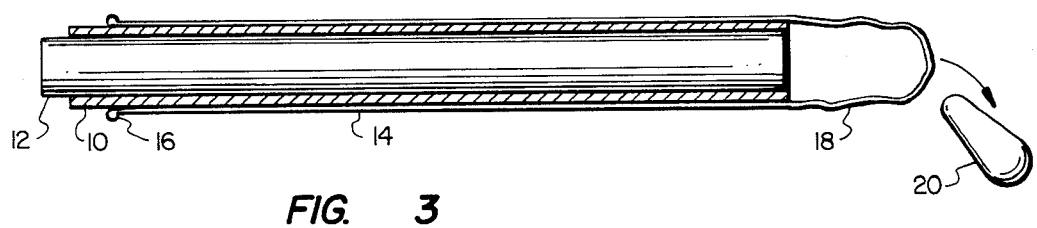
FIG. 3 is a sectional view of the improved vaginal medication application apparatus of the present invention, after dispensing a vaginal suppository.

Referring now to FIG. 3, there is depicted a sectional view of the novel vaginal medication application apparatus of the present invention Piston means 12 is depicted after having been inserted fully into tubular applicator 10. Piston means 12, after insertion into tubular applicator 10 will outwardly extend closed end 18 of tubular membrane 14, thus expelling vaginal suppository 20. After utilization, tubular membrane 14 may be removed from hollow tubular applicator 10 and discarded, thus preventing possible reinfection or contagion upon subsequent utilizations of tubular applicator 10. In this manner, tubular applicator 10 may be constructed of a material which would not ordinarily be utilized in a reusable applicator, in that the sanitary condition of tubular applicator 10 may be maintained without requiring traditional disinfecting techniques.

Figure 4:
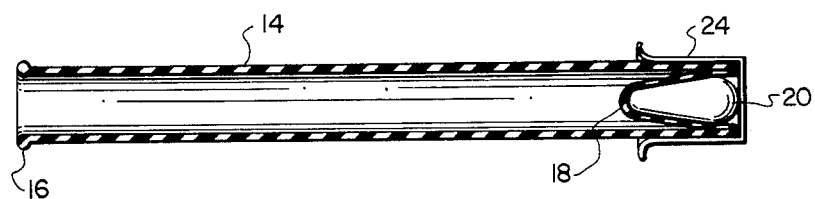
FIG. 4 is a sectional view of the improved vaginal medication packaging apparatus of the present invention.

Referring now to FIG. 4, there is depicted one embodiment of a novel apparatus for the packaging of intravaginal medication, utilizing the tubular membrane 14 of the present invention. Membrane 14 has been depicted having a greater cross-section than would ordinarily be utilized, merely for illustrative purposes. As discussed above, tubular membrane 14 includes an open end 16 and a closed end 18. Closed end 18 is axially depressed within tubular membrane 14 to form a suitable cavity into which the vaginal medication may be placed. When utilized as a packaging base for vaginal medication, the apparatus will also include sealing means 24, which may be a plastic, paper, or latex rubber based sealing cap which completely encloses vaginal medication 20 within a sanitary cavity, thus enhancing the sanitary condition of the medication as it is received by the consumer.

Although the invention has been described with reference to a specific embodiment, this description is not meant to be construed in a limiting sense. Various modifications of this disclosed embodiment as well as alternative embodiments of the invention will become apparent to persons skilled in the art upon reference to the description of the invention. It is therefore contemplated that the appended claims will cover any such modifications or embodiments that fall within the true scope of the invention.

What is claimed is:
1. Apparatus for use in the repetitive intravaginal application of medication comprising:
 a reversable hollow tubular member suitable for vaginal insertion;
 a separate, disposable flexible tubular membrane having a closed end and an open end and adapted to be disposed in sleeved relationship with and along the exterior surface of said hollow tubular member covering substantially all of said hollow tubular member, said closed end adapted to be axially depressed into a first end of said hollow tubular member wherein a cavity is formed within said first end of said hollow tubular member for receiving medication; and
 a piston member, adapted to be inserted into a second end of said hollow tubular member for outwardly extending said closed end of said tubular membrane whereby said medication may be dispensed without contamination of said hollow tubular member and said piston member.

2. The apparatus for use in the repetitive intravaginal application of medication according to claim 1 wherein said tubular member is constructed of plastic.

3. The apparatus for use in the repetitive intravaginal application of medication according to claim 1 wherein said flexible tubular membrane is constructed of a thin pliable plastic film.

4. The apparatus for use in the repetitive intravaginal application of medication according to claim 3 wherein said flexible tubular membrane is constructed of a thin polyethylene film.

* * * * *